US006448387B1

(12) United States Patent
Slater et al.

(10) Patent No.: US 6,448,387 B1
(45) Date of Patent: Sep. 10, 2002

(54) POLYMERIC ARRAYS ADAPTED FOR HIGH EXPRESSING POLYNUCLEOTIDES

(75) Inventors: Caroline Slater, Holliston; Jeffrey P Cambray, Lowell; Robert A. Obar, Walpole, all of MA (US)

(73) Assignee: Monsanto Technology, LLC, St. Louis, MO (US)

( * ) Notice: Subject to any disclaimer, the term of this patent is extended or adjusted under 35 U.S.C. 154(b) by 0 days.

(21) Appl. No.: 09/740,297

(22) Filed: Dec. 18, 2000

(51) Int. Cl.[7] .......................... C07H 21/04; C12Q 1/68; C12Q 1/70; C12M 1/36; G01N 15/06
(52) U.S. Cl. ................ 536/23.1; 536/24.31; 536/24.32; 435/5; 435/6; 435/283.1; 435/287.1; 435/287.2; 435/288.7; 422/50; 422/61; 422/68.1; 422/82.05
(58) Field of Search .............................. 435/6, 5, 287.2, 435/288.7, 287.1, 283.1; 536/23.1, 24.31, 24.32; 422/50, 61, 68.1, 82.05

(56) References Cited

U.S. PATENT DOCUMENTS

| | | | | |
|---|---|---|---|---|
| 5,143,854 A | * | 9/1992 | Pirrung et al. | ............... 435/518 |
| 5,807,522 A | * | 9/1998 | Brown et al. | ................. 422/50 |
| 6,040,138 A | * | 3/2000 | Lockhart et al. | ............... 435/6 |
| 6,280,946 B2 | * | 8/2001 | Hyldig–Nielsen et al. | |

OTHER PUBLICATIONS

Tanaka et al. "Genome–side expressionprofilingof mid–g-estation placenta and embryo using a 15,000 mouse developmental cDNA microarray" Proc. Natl. Acad. Sci. USA 2000, 97(16): 9127–9132.*

* cited by examiner

Primary Examiner—Stephanie Zitomer
Assistant Examiner—B J Forman
(74) Attorney, Agent, or Firm—Thomas E Kelley; Lawrence M. Lavin, Jr.; Dennis R. Hoerner, Jr.

(57) ABSTRACT

Arrays of polynucleotide or polypeptide target molecules immobilized on a surface of a substrate where the target molecules are arranged in the array according to intensity of organism expression of cognate probe molecules which hybridize to the target molecules. For instance, target molecules having a higher than average indicia of hybridization, e.g. at least a factor of 2, are segregated at a peripheral region of the substrate and at a lower surface density. Preferred arrays can contain animal, plant or microorganism target molecules including *Aspergillus nidulans*. Diagnostic arrays can comprise targets from mixed species, e.g. human, mouse and virus; plant breeding arrays can comprise targets from mixed plants, e.g. *Arabidopsis thaliana*, maize, soy, cotton, wheat, rice, canola and potato.

7 Claims, 4 Drawing Sheets

POLYMERIC ARRAYS ADAPTED FOR HIGH EXPRESSING POLYNUCLEOTIDES

Disclosed herein are arrays of polymeric targets useful for evaluating the expression of polynucleotides and polypeptides, and methods of making and using such arrays.

BACKGROUND OF THE INVENTION

Arrays of binding agents, such as nucleic acid molecules, have become an increasingly important tool in the biotechnology industry and related fields. These arrays typically comprise a plurality of binding agents, e.g. DNA or protein, deposited onto a solid substrate surface in a precise array or pattern. Such arrays find use in a variety of applications, including gene discovery, genomic research and bioactive compound screening. One important use of arrays is in the analysis of differential gene expression, where the expression of genes in different cells, normally a cell of interest and a control, is compared and any discrepancies in expression are identified. In such assays, the presence of discrepancies indicates a difference in genes expressed in the cells being compared. Such information is useful for the identification of the types of genes expressed in a particular cell or tissue type in a known environment.

The economics of arrays favors a high density design criteria providing microarrays for detection of transcription events for a large number of genes provided that the target molecules are sufficiently separated so that the intensity of the indicia of a binding event associated with highly expressed probe molecules does not overwhelm and mask the indicia of neighboring binding events. Some genes are inherently high expressors, e.g. transcribe mRNA at significantly higher quantities, as compared to other genes which are inherently low expressors. For instance, differences in transcription levels of about an order of magnitude or more are not uncommon. As a result the indicia of binding events on an array from a high expresser intensity probe molecule can obliterate indicia from up to eight neighboring target molecules or more in a rectangular grid.

One object of this invention is to provide arrays in higher density of target molecules without interference from binding events associated with high expresser probe molecules.

Another object of this invention is to provide methods of transcription profiling using high density arrays for full genome profiling without interference from binding events associated with high expressor probe molecules.

These and other objects of the invention will be apparent from the following description and claims.

SUMMARY OF THE INVENTION

This invention provides sets of polynucleotide or polypeptide target molecules immobilized in an array on a surface of a substrate where the target molecules are selected for their capability to hybridize with probe molecules expressed by an organism of interest. A subset of the target molecules is arranged according to intensity at which the organism expresses a set of cognate probe molecules.

In one embodiment the probe molecules comprise a first set of probe molecules which, at a fixed set of conditions, are on average expressed by the organism at a higher concentration than other probe molecules. The first set of target molecules which hybridize to the first set of higher expressed probe molecules is segregated from other target molecules which hybridize to the other probe molecules. In a preferred embodiment the first set of target molecules is segregated at a peripheral region of the substrate. In another preferred embodiment the average expression intensity of the first set of higher expressed probe molecules is at least a factor of 2 greater than the average expression intensity of the other probe molecules. In still another embodiment of the invention the surface density of segregated target molecules on the substrate is less than about 0.5 times the surface density of the other target molecules.

In one embodiment of the invention the arrays are microarrays of single-stranded cDNA target molecules. Such microarrays are especially useful for hybridizing with labeled mRNA probes, e.g. for transcription profiling studies, and can be prepared for a variety of organisms, e.g. animal, plant and/or microorganism.

The invention also provides methods for fabricating arrays of target molecules by segregating to a peripheral region of a substrate target molecules which have been identified by higher than average indicia of hybridization for certain conditions of probe molecule expression by an organism of interest.

This invention also provides a method for detecting a binding event between a naturally expressed probe molecule and a target molecule immobilized in an array on a substrate. The method comprises (a) contacting an array of target molecules immobilized on a substrate with a solution of a plurality of probe molecules expressed by an organism, where the target molecules are arranged on the substrate according to expression level; and (b) detecting binding events between target molecules and probe molecules where the indicia of binding for probe molecules expressed at higher concentration does not interfere with indicia of binding for probe molecules expressed at lower concentration. In preferred embodiments of the method the probe molecules are labeled with radioactive, fluorescent and enzymatic labels.

DEFINITIONS

Figure 1:
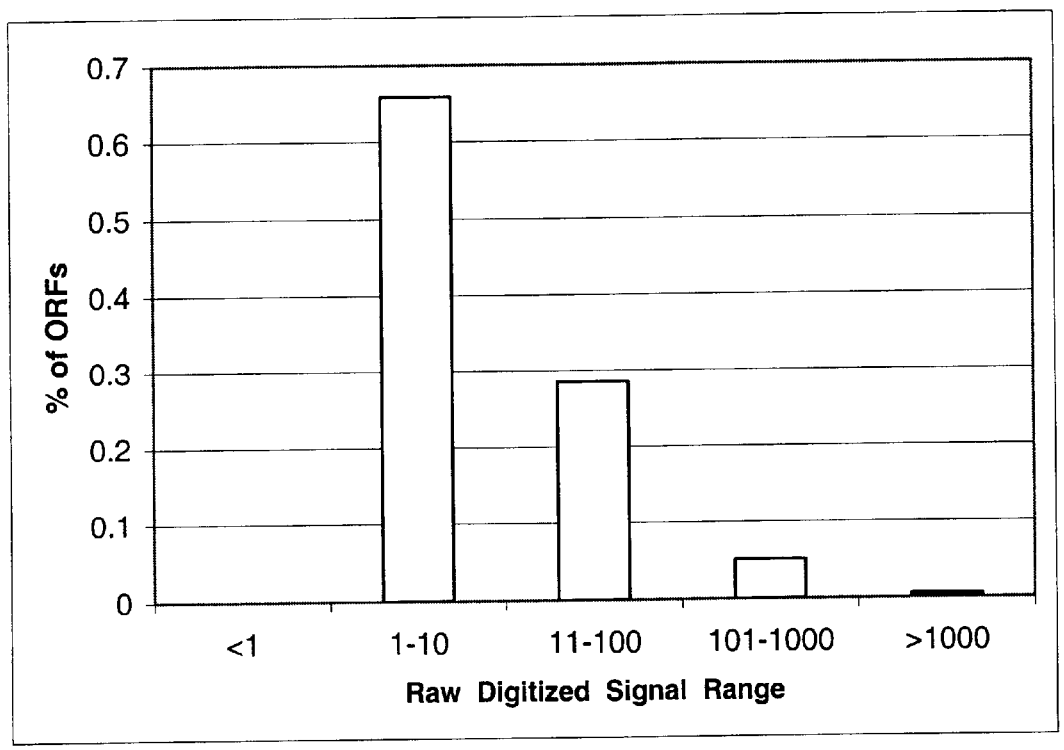
FIG. 1 is a graphical representation of gene distribution as a function of expression level for *Aspergillus nidulans* in one environment.

As used herein (a) "substrate" means a solid material for supporting target molecules; substrates can be flexible such as nylon membranes or rigid such as glass sheet or silicon wafer; nylon membranes are common, porous supports for microarrays;

(b) "target" means a known molecule, e.g. polynucleotide or polypeptide, which is capable of hybridizing to a cognate probe, i.e. a complementary nucleotide or corresponding antibody;

(c) "probe" means an unknown molecule or more typically a mixture of unknown molecules which are labeled, typically with a fluorescent, radioactive or enzymatic label; probes from one source typically have a common label; mixtures of probes from multiple sources may be labeled with differentiating labels, e.g. different color dyes or mixed detection labels; a preferred label is $^{33}$P nucleotides which can be readily incorporated into mRNA;

(d) "spotted element" means an amount of target molecule, e.g. polynucleotide or polypeptide in a grid position on an array; the target molecule can be a deposited molecule or a molecule which is synthesized at the position;

(e) "array" means rows and columns of spotted molecule elements located on a membrane including rows and columns of subarrays; e.g. a useful array can comprise 16×24 rows/columns of a sub array of spotted molecule elements;

(f) "sub array"=rows and columns of grid positions within a grid element, e.g. a 16×16, 25×25, 4×4 or 5×5 rows/columns of spotted molecule elements;

(g) "microarray" means a high density array, e.g. comprising a surface density of at least 10 distinct and separated target molecules per square centimeter and up to $10^3$ or more distinct and separated spotted target molecules per square centimeter;

(h) "array density" means the number of distinct and separated spots on an array divided by area of array, e.g. a nylon membrane with an array area of 7.5 cm×11 cm and DNA elements spotted in a 16×24/5×5 array/subarray pattern has 9600 spots/82.5 square cm (or 116 spots/cm$^2$).

(i) "expression intensity" means the level of expression (e.g. transcribed/translated ) of cellular molecules, e.g. mRNA or protein, as measured by hybridization intensity;

(j) "high expresser" means an expressed molecule having an Expression Intensity in the top 10% of all molecules expressed, more preferably in the top 5%, even more preferably in the top 3% of all molecules expressed. Some genes are inherently high expressors; some genes are inherently low expressors; and some genes can be either high or low expressors, e.g. in response to stimuli. The relative number of high expressors varies by organism. For instance, microorganisms have relatively small genomes and can have a relatively higher percentage of all genes actively expressing molecules at any time. More complex organisms such as plants and animals have relatively large genomes and gene expression is dependent on selected tissue, stage in life cycle, temporal activity, etc.

(k) "polypeptide" means a protein or part of a protein comprising at least 6 amino acid units, more preferably at least 8 amino acid units, most preferably at least 10 amino acid units;

(l) "nucleic acid molecule" means a polymer composed of nucleotides, e.g. deoxyribonucleotides or ribonucleotides;

(m) "RNA" means a polymeric nucleic acid molecule composed of ribonucleotides;

(n) "DNA" means a polymeric nucleic acid molecule composed of deoxyribonucleotides, e.g. cDNA molecules;

(o) "oligonucleotide" means a single stranded nucleic acid molecule, typically in the range of 10 to 400 nucleotides in length, more commonly at least about 20 to about 100 nucleotides in length;

(p) "polynucleotide" means a single or double stranded polymeric nucleic acid molecule ranging from an oligonucleotide to a genomic region;

(q) "cognate molecules" means molecules that hybridize under defined stringency conditions due to a natural relationship, e.g. ancestry or homology, for instance, the RNA which specifically hybridizes to its source DNA and the polypeptide which specifically hybridizes to its antibody.

(r) "segregated" means set apart from the rest of the class; for instance segregated targets on an array can be at one or more peripheral edges of the array or at an islet of targets within the array;

DESCRIPTION OF SPECIFIC EMBODIMENTS

This invention provides arrays having polynucleotide or polypeptide target molecules arranged on a surface of a substrate according to intensity of expression of cognate probe molecules by an organism under the conditions being studied. In defining arrays of this invention a set of cognate probe molecules comprises one or more subsets of probe molecules which are on average expressed by an organism under the conditions being studied at a higher concentration than other probe molecules and one or more subsets of probe molecules which are on average expressed by the organism at a lower concentration that the highly expressed probe molecules. At least one first set of target molecules which hybridize to the at least one first set of highly expressed cognate probe molecules is segregated from other target molecules on the array. The at least one first set of target molecules is preferably segregated at a peripheral region of the substrate, e.g. in peripheral rows or columns of gridded subarrays. The target molecules which hybridize to high expresser probes are identified and selected based on the indicia of hybridization events, e.g. on a random or predetermined assembled array of target molecules. Target molecules which are cognates of high expressor probes will preferably include target molecules for which the exhibited indicia of probe binding overwhelms the indicia of binding events at neighboring targets. The cognate probe molecules of target molecules selected for segregation will have an average expression intensity of at least a factor of 2 greater than the average expression intensity of other probe molecules. The surface density of segregated target molecules on a substrate is preferably less than about 0.5 times the surface density of other target molecules. It is understood that the selection of segregated target molecules may be dependent on the conditions in which probe molecules are expressed, e.g. environmental response or stage in life cycle of the organism under study. That is, different subsets of selected segregated arrays may useful for different assays.

Thus, one aspect of the invention provides methods for fabricating arrays of target molecules adapted to hybridize to probe molecules by depositing in segregated regions of a surface of a substrate a subset of target molecules which hybridize to high expressor labeled probe molecules expressed by an organism of interest. The method comprises obtaining and hybridizing to an original array of target molecules an original set of labeled probe molecules from the organism under fixed conditions of probe molecule expression. The indicia of hybridization are analyzed to provide an average indicia of hybridization and to identify loci of target molecules providing an indicia of hybridization which is at least multiple of the average indicia of hybridization, e.g. at least twice the average indicia or more, for instance five or ten times average. A useful multiple is that which interferes with a reading of indicia at neighboring loci. Subsequent arrays of target molecules which are useful for transcription profiling of the organism at the fixed conditions are prepared by segregating the target molecules identified at loci or high indicia of hybridization.

A feature of the arrays of this invention is that target members of the array are arranged with respect to the intensity in which the organism under study expresses the hybridizing probe molecules. In some cases it is preferable that each array comprise target molecules obtained from or based on the same source, e.g. the same organism or at least a common tissue in an organism. Arrays can be prepared for use with classes of organisms, e.g. animals, plants or microorganisms including virus, bacteria and fungus. Single species arrays can be prepared from target molecules from a single species including an animal such as human, mouse, cow, pig, sheep, goat, chicken, salmon, trout, catfish, monkey, dog, horse and fruit fly, a plant such as maize, soybean, cotton, wheat, canola, sugar beet, potato, rice and *Arabidopsis thaliana*, a microorganism such as *Aspergillus nidulans, E. coli*, and *Agrobacterium tumefaciens*. Tissue specific arrays can comprise target molecules from a common tissue from a variety of species, e.g. root tissue from a variety of plants. Useful arrays, e.g. for diagnostic applications, can comprise target molecules from multiple species, e.g. human, pig, mouse and/or virus such as a papilloma virus or a human immunodeficiency virus. Arrays with target molecules from single species can be used with probe molecules from the same species or a different species or a mixture or species, e.g. due to the ability of cross species homologous genes to hybridize.

In such arrays of spotted cDNA elements the target molecules can comprise of about $10^7$ (10 million) to $10^{11}$ (10 billion) copies of single stranded DNA immobilized on a glass array and about $10^8$ (100 million) to $10^{12}$ (one trillion) copies immobilized on a nylon membrane. In arrays of deposited elements of target molecules on flexible nylon membrane supports for use with probe molecules of $^{33}$P-labeled mRNA, the deposited elements of target molecules which bridge to low expressor probes can be arranged in rectangular grids of a density of at least about 50 deposited elements per square centimeters, preferably at least about 80 or more, e.g. at least about 100, elements per square centimeter, in some cases even more preferably at least about 150 or more, e.g. at least about 300 elements per square centimeter. Densities on other substrates, e.g. glass can be significantly higher, on the order or 1000 or 10,000 elements per square centimeter. For target molecules which hybridize to high expresser probes the density will be lower, e.g. preferably not more than about 75% or lower, say not more than about 50%, of the target density for targets which hybridize to low expressor probes. In the case of arrays on flexible nylon membrane supports the density of target molecules which hybridize to high expresser probes will often be less than about 100 elements per square centimeter, more preferably not more than about 80 or fewer, say about 60, elements per square centimeter, in some cases even more preferably not more than about 45 or fewer, say about 30, elements per square centimeter. In one embodiment of this invention comprising an array on flexible nylon membrane supports, the density of target molecules which hybridize to low expresser probes of $^{33}$P-labeled MRNA is about 116 elements per square centimeter and the density of target molecules which hybridize to high expressor probes is about 58 elements per square centimeter.

The probe molecules are labeled and the detecting comprises detecting the presence of the label which is preferably selected from the group consisting of radioactive, fluorescent and enzymatic labels; a preferred radioactive label is a $^{33}$P-containing nucleotide such as dUTP, dCTP, dGTP or dATP. In the method when probe molecules are radioactively labeled, unbound probe molecules are washed from said substrate after hybridization and prior to detecting.

In the arrays of this invention, the target molecules are immobilized on the surface of a substrate, e.g. a flexible support such as a nylon membrane or rigid support such as a glass sheet or silicon wafer. By immobilized is meant that the target molecules maintain their position relative to the support under hybridization and washing conditions. As such, the target molecules can be covalently or non-covalently stably associated with the substrate material or a coating of a binding or linkage material selected from among those well known in the art. Examples of non-covalent association include non-specific adsorption, specific binding through a specific binding pair member covalently attached to the support surface, and entrapment in a matrix material, e.g. a hydrated or dried separation medium, which presents the target in a manner sufficient for binding, e.g. hybridization, to occur. Examples of covalent binding include covalent bonds formed between the target and a functional group present on the surface of the support, e.g. -H, where the functional group may be naturally occurring or present as a member of an introduced linking group.

Although the shape of the substrates can vary, it is common for the array to be disposed in a rectangular area on a planar surface of the substrate to facilitate registration of target molecules in an addressable array. Generally, the overall dimensions of an array are in the range of 1 to 40 cm. Target molecules are deposited in small footprint, isolated spots. For high density microarrays each spot may contain up to about $10^{11}$ copies of the target molecule, e.g. about $10^8$ to $10^{11}$ strands of single-stranded cDNA or a fragment of cDNA. Spotted elements can be placed on arrays by depositing target molecules in a grid pattern onto a substrate or fabricating oligonucleotide or peptide sequences in situ on a substrate. Spotted elements can be applied in a high density matrix pattern of up to about 300 non-identical spots of target molecules per square centimeter or higher, e.g. up to about 1000 or even 10000 per square centimeter. See, for instance:

U.S. Pat. No. 5,202,231 for methods of sequencing of genomes by hybridization of oligonucleotide probes;

U.S. Pat. Nos. 5,384,261; 5,405,783; 5,424,186; 5,445,934; 5,556,752 and 5,599,695 for methods for synthesizing immobilized polypeptides and oligonucleotides in an array on a substrate;

U.S. Pat. No. 5,429,807 for methods for synthesizing biopolymer arrays;

U.S. Pat. No. 5,561,071 for arrays of immobilized DNA binding proteins;

U.S. Pat. No. 5,807,522 for methods for fabricating microarrays of spotted polynucleotides or polypeptides at high density;

U.S. Pat. No. 5,800,992 for methods for using arrays of polynucleotides to detect nucleic acid sequences;

U.S. Pat. No. 6,004,755 for methods for quantitative microarray hybridization assays; and U.S. Pat. No. 6,087,102 arrays of immobilized polymeric targets arranged according to size;

British Patent Application GB 2318791A for arrays of single-stranded DNA immobilized on a solid support; and European Patent application EP 0 848 067 A2 for computer-aided techniques for analyzing biological sequences, e.g. hybridization intensities, the disclosures of all of which are incorporated herein by reference in their entireties.

Protocols for isolating nucleic acids, proteins and their fractions from cells, tissues, organs and whole organisms are described in: Maniatis et al., Molecular Cloning: A Laboratory Manual (Cold Spring Harbor Press)(1989); Scopes R., Protein Purification. Principle and Practice (Springer-Verlag)(1994); and Deutscher, Guide to Protein Purification (Academic Press)(1990), all of which are incorporated herein by reference in their entireties. Such methods typically involve subjection of the original biological source to one or more of tissue/cell homogenization, nucleic acid/protein extraction, chromatography, centrifugation, affinity binding and the like.

The subject arrays or devices into which they are incorporated may conveniently be stored following fabrication for use at a later time. Under appropriate conditions, the subject arrays are capable of being stored for at least about 6 months and may be stored for up to one year or longer. The subject arrays are generally stored at temperatures between about −20° C. to room temperature, where the arrays are preferably sealed in a plastic container, e.g. bag, and shielded from light.

Applications in which the subject arrays find particular use are expression analysis applications. Such applications generally involve the following steps: (a) preparation of probe, e.g. attaching a label to a plurality of expressed molecules; (b) contact of probe with the array under conditions sufficient for probe to bind with corresponding target, e.g. by hybridization or specific binding; (c) removal of unbound probe from the array; and (d) detection of bound probe. Each of these steps will be described in greater detail below.

Probe preparation depends on the specific nature of the probe, e.g. whether the probe is a polynucleotide or polypeptide. Polynucleotide probes may be RNA or DNA, as well as hybridizing analogues or mnimetics thereof, e.g. nucleic acids in which the phosphodiester linkage has been replaced with a substitute linkage, such as a phosphorothioate, methylimino, methylphosphonate, phosphoramidite, guanidine and the like; and nucleic acids in which the ribose subunit has been substituted, e.g. hexose phosphodiester, peptide nucleic acids; and the like. The probe will have sufficient complementarity to its target to provide for the desired level of sequence specific hybridization. Polynucleotide probes can range from about 10 to 2000 nucleotides where short probes in the range of about 15 to 100 nucleotides are commonly called oligonucleotide probes. Although polynucleotide probes may be double stranded, single stranded probes are preferred.

Polypeptide probes that find use in the subject invention include: antibodies, e.g. polyclonal, monoclonal, and binding fragments thereof; peptides with high affinity to the target, as well as analogues and mimetics thereof; ligands, receptors, and the like.

Generally, the probe molecule will be labeled to provide for detectability in the detection step. By labeled is meant that the probe comprises a member of a signal producing system and is thus detectable, either directly or through combined action with one or more additional members of a signal producing system. Examples of directly detectable labels include radioactive isotopes and fluorescent materials incorporated into or covalently bonded to the probe molecule. More particularly the label can comprise a nucleotide monomeric unit, e.g. dNTP of a primer, or a photoactive or chemically active derivative of a detectable label which can be bound to a functional part of the probe molecule. Radioactive isotope label elements include $^{32}P$, $^{33}P$, $^{35}S$, $^{125}I$, and the like with $^{33}P$ being especially preferred. Fluorescent label elements include coumarin and its derivatives, e.g. 7-amino-4-methylcoumarin, amninocoumarin, bodipy dyes, such as Bodipy FL, cascade blue, fluorescein and its derivatives, e.g. fluorescein isothiocyanate, Oregon green, rhodamine dyes, e.g. Texas red, tetramethylrhodamine, eosins and erythrosins, cyanine dyes, e.g. Cy3 and Cy5, macrocyclic chelates of lanthanide ions, fluorescent energy transfer dyes, such as thiazole orange-ethidium heterodimer, TOTAB, etc. Labels may also be members of a signal producing system that act in concert with one or more additional members of the same system to provide a detectable signal. Illustrative of such labels are members of a specific binding pair, such as ligands, e.g. biotin, fluorescein, digoxigenin, antigen, polyvalent cations, chelator groups and the like, where the members specifically bind to additional members of the signal producing system, where the additional members provide a detectable signal either directly or indirectly, e.g. antibody conjugated to a fluorescent moiety or an enzymatic moiety capable of converting a substrate to a chromogenic product, e.g. alkaline phosphatase conjugate antibody; and the like. Additional labels of interest include those that provide for signal only when the probe with which they are associated is specifically bound to a target molecule, where such labels include: "molecular beacons" as described in Tyagi & Kramer, Nature Biotechnology (1996) 14:303 and EP 0 070 685 B1. Other labels of interest include those described in U.S. Pat. No. 5,563,037; WO 97/17471 and WO 97/17076. A preferred label for polynucleotide probes is $^{33}P$ which is incorporated into copies of RNA via a radiolabeled dNTP, e.g. dUTP.

This invention also provides methods for detecting binding events between naturally expressed probe molecules and target molecules in an array. The methods comprise (a) contacting an array of target molecules immobilized on a substrate with a solution of a plurality of probe molecules expressed by an organism of interest, where the target molecules are arranged on the substrate according to expression level; and (b) detecting binding events between target molecules and probe molecules where the indicia of binding for probe molecules expressed at higher concentration does not interfere with indicia of binding for probe molecules expressed at lower concentration. In certain preferred aspects of the methods the binding event comprises hybridization between complementary polynucleotides, e.g. MRNA and cDNA, where the organism of interest is a plant selected from the group consisting of *Arabidopsis thaliana*, maize, soy, cotton, wheat, rice, canola and potato. In another preferred aspect of the methods of this invention the binding event comprises hybridization of fungal polynucleotides where the array comprises cDNA derived from the filamentary fungus *Aspergillus nidulans* (also known as *Emericella nidulans*). To analyze the transcription of fungal genes a percent of the high expressor genes corresponding to target molecules segregated on said array are selected from the genes which have a nucleic acid sequence which has between 60 and 100 percent identity to sequences in the group consisting of SEQ ID NO: 1 to SEQ ID NO: 272 and complements thereof.

In the method the probe molecule is contacted with the array under conditions sufficient for binding between the probe and the target of the array. For example, where the probe and target are nucleic acids, the probe will be contacted with the array under conditions sufficient for hybridization to occur between the probe and target, where the hybridization conditions will be selected in order to provide for the desired level of hybridization specificity. For polypeptide probes, conditions will be selected to provide for specific binding between the probe and its target.

Contact of the array and probe involves contacting the array with an aqueous medium comprising the probe. Contact may be achieved in a variety of different ways depending on specific configuration of the array. For example, contact may be accomplished by simply placing the array in a container comprising the probe solution, such as a polyethylene bag, and the like. In other embodiments where the array is entrapped in a separation media bounded by two rigid plates, the opportunity exists to deliver the probe via electrophoretic means. Alternatively, where the array is incorporated into a biochip device having fluid entry and exit ports, the probe solution can be introduced into the chamber in which the pattern of target molecules is presented through the entry port, where fluid introduction could be performed manually or with an automated device. In multi-well embodiments, the probe solution will be introduced in the reaction chamber comprising the array, either manually, e.g. with a pipette, or with an automated fluid handling device. For flexible nylon substrate microarrays it is convenient to roll the nylon substrate into a roll for insertion into a vial where a small volume of probe solution can efficiently contact target through shaking.

Contact of the probe solution and the targets will be maintained for a sufficient period of time for binding between the probe and the target to occur. Although dependent on the nature of the probe and target, contact will generally be maintained for a period of time ranging from about 10 min to 24 hrs, usually from about 30 min to 12 hrs and more usually from about 1 hr to 6 hrs.

Following binding of probe and target, the resultant hybridization patterns of labeled probe may be visualized or detected in a variety of ways, with the particular manner of detection being chosen based on the particular label of the nucleic acid, where representative detection means include scintillation counting, autoradiography, fluorescence measurement, calorimetric measurement, light emission measurement and the like. The method may or may not further comprise a non-bound label removal step prior to the detection step, depending on the particular label employed on the probe. For example, in homogenous assay formats a detectable signal is only generated upon specific binding of probe to target. As such, in homogenous assay formats, the hybridization pattern may be detected without a non-bound label removal step. In other embodiments, the label employed will generate a signal whether or not the probe is specifically bound to its is target. In such embodiments, the non-bound labeled probe is removed from the support surface. One means of removing the non-bound labeled probe is to perform the well known technique of washing, where a variety of wash solutions and protocols for their use in removing non-bound label are known to those of skill in the art and may be used. Alternatively, in those situations where the targets are entrapped in a separation medium in a format suitable for application of an electric field to the medium, the opportunity arise to remove non-bound labeled probe from the target by electrophoretic means. With radioactive labeled probes it is important to remove the unbound probe. The hybridization binding events can be read by exposure of a radioactive-labeled hybridized array to photographic film or preferably a digitizer for simultaneously reading and storing the intensity of the hybridization events.

The target expression level in the particular tissue being analyzed can be derived from the intensity of the detected signal. To ensure that an accurate level of expression is derived, it is useful to provide the array with calibrating elements of blank and standard targets dispersed throughout the array. A standard target can comprise a fixed amount of a mixture of genomic DNA from the organism of interest. In the case of arrays of *Aspergillus nidulans* a useful generic target comprises about 50 picograms of a mixture of genomic DNA. A similar amount (5–500 picograms) of genomic DNA can be used in standard targets for arrays based on other organisms of interest to provide a constant detectable amount of probe at multiple locations in the array. Alternatively, a standard spot can comprise a fixed amount of a $^{33}$P-containing compound which is designed to be non-hybridizing to natural probes. The use of blank and standard elements assists in calibrating and correlating hybridization signals which may be processed at different exposure times and/or with multiple arrays and/or with different experiments.

The arrays of this invention find can be used in a variety of different gene expression analysis applications, including transcription profiling differential expression analysis of diseased and normal tissue; different tissues or subtypes; tissues and cells under different condition states, like predisposition to disease, age, exposure to pathogens or toxic agents, etc.; and the like.

The following examples are offered by way of illustration and not by way of limitation.

EXAMPLE 1

This example illustrates the preparation of a cDNA microarray which is useful for transcription profiling by hybridization of RNA. A microarray comprising cDNA is prepared by attaching polynucleotides representing genes of *Aspergillus nidulans* to defined areas on the surface of a negatively-charged, nylon support membrane. The polynucleotides are amplified cDNA molecules in the range of about 200 to 2000 nucleotide bases in length. Spotted elements of separated polynucleotide are attached in each of the 9600 grid positions of 5×5 subarrays in an array pattern of 16×24, where spotted targets have a nominal diameter of about 0.5 mm and the target density is 116 spotted targets per square centimeter.

Figure 3:
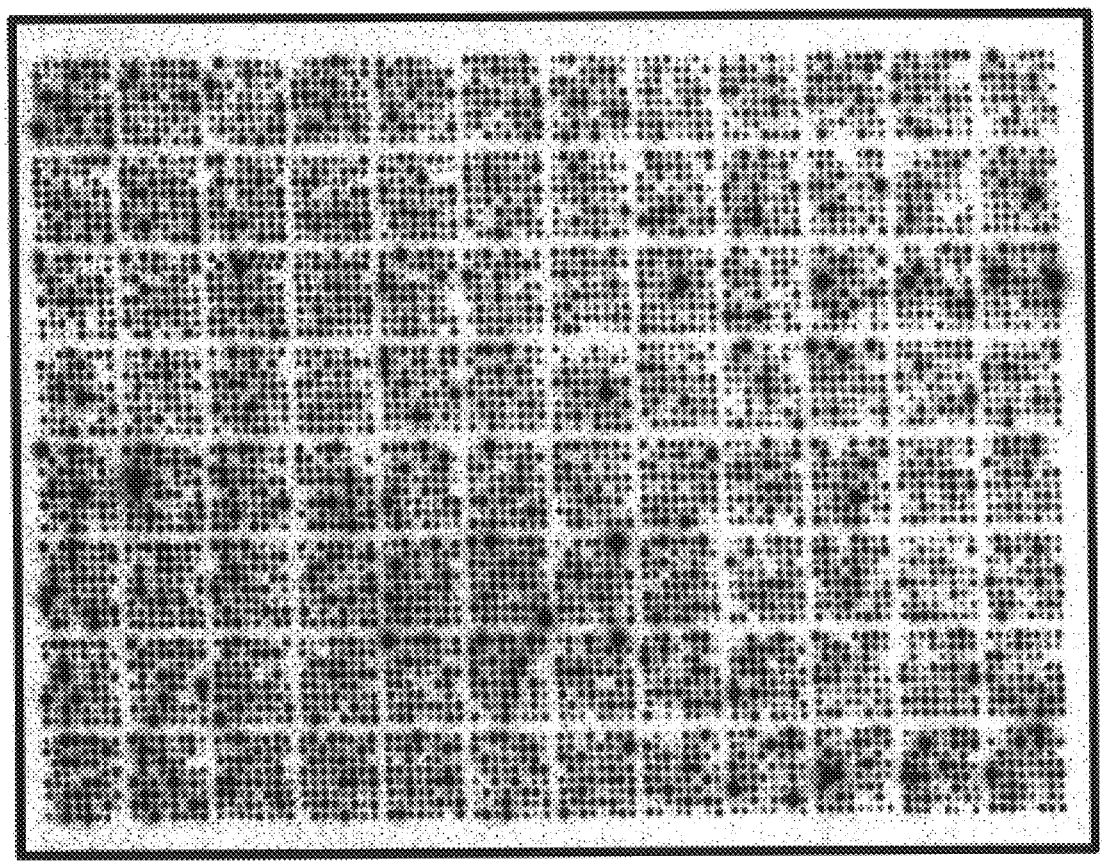
FIG. 3 shows a developed film image of radioactive label for an array with randomly spotted target molecules.

A sample of *Aspergillus nidulans* tissue is mechanically ground while frozen in liquid nitrogen. The mRNA is isolated from ground tissue using commercially available reagents, such Dynabeads™ mRNA DIRECT™ from Dynal Biotech, Oslo, Norway. The isolated mRNA is labeled by oligonucleotide priming, e.g. with a Superscript™ First Strand Synthesis System for RT PCR, with labeled dCTP, from Invitrogen Corporation, Carlsbad, Calif. The labeled first strand cDNA is mixed with 2.5 ml of TES/NaCl solution and allowed to hybridize to a microarray in a 50 ml chamber rotating at 65° C. in a hybridization oven. The unbound portion of the cDNA solution is rinsed off the microarray by two 1 hour washings with 2×SSC at 65° C. The microarray is rinsed again for 1 hour in 2×SSC at 37° C., dried and placed in contact with a Fuji Phosphoimager™ imaging screen. After an appropriate exposure time the array image is read as a digital file representing the hybridization intensity from each array element which is proportional to the steady state mRNA in the tissue. FIG. 3 is a copy of an imaging screen showing regions of high intensity where the indicia of hybridization events for high expressing probes blooms over the signal of neighboring targets effectively interfering with the ability to read the level of hybridization events at neighboring targets.

EXAMPLE 2

Figure 2:
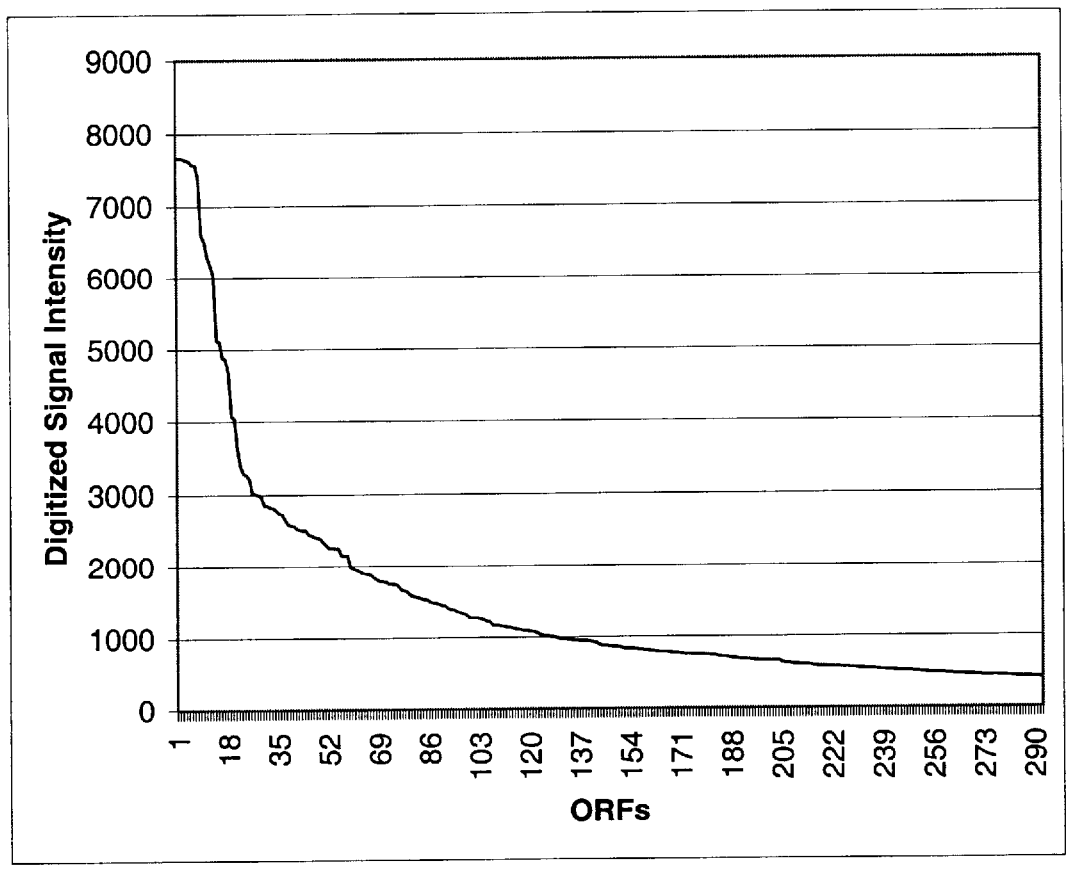
FIG. 2 is a graphical representation of expression level for a group of 300 high expressing genes for *Aspergillus nidulans* in one environment.

This example illustrates the design and fabrication of a microarray having segregated target molecules. FIG. 1 shows the relative hybridization signal for groups of *Aspergillus nidulans* genes. About 66% of the genes have a low level of hybridization signal, e.g. in the relative range of 1–10, indicating low expression. About 28.5% have a moderate hybridization signal, e.g. in the relative range of 10–100, indicating moderate expression. About 5% have a high hybridization signal, e.g. in the relative range of 100 to 1000, indicating high expression. And, about 0.5% have a very high hybridization signal, e.g. in the relative range of greater than 1000, indicating very high expression. With random spotting of target molecules the hybridization signal from high expressors interferes with signals from adjacent targets. FIG. 2 shows the relative hybridization signal for the top 300 high expressing genes.

The target molecules for 272 of the top 300 high expressing genes are located in a new array in a single peripheral row at lower spatial density, i.e. in about 11 of the 25 spots of a 5×5 subarray. Such relocation permits development of different parts of the array at different exposure times. For instance, the high expressing rows containing higher levels of radioactive label is read by exposing a radioactive hybridized array for a relatively short time as compared to the relatively longer exposure time to develop the radioactive label signal from the hybridized events for the low expressing genes.

The array is provided with a plurality of blank (e.g. buffer solution containing no DNA) and standard (e.g. 500 nanograms of genomic DNA) elements. The standard elements are prepared by depositing about 50 nanoliters of a mixture of genomic DNA at lo nanograms per microliter. The array comprises target molecules of about $10^8$ to $10^{11}$ copies of single stranded DNA in spotted elements on a flexible nylon membrane wherein said spotted elements are in a rectangular grid of a density of about 116 elements per square centimeter for low expressor probes and a density of about 58 elements per square centimeter for high expressor probes.

EXAMPLE 3

Figure 4:
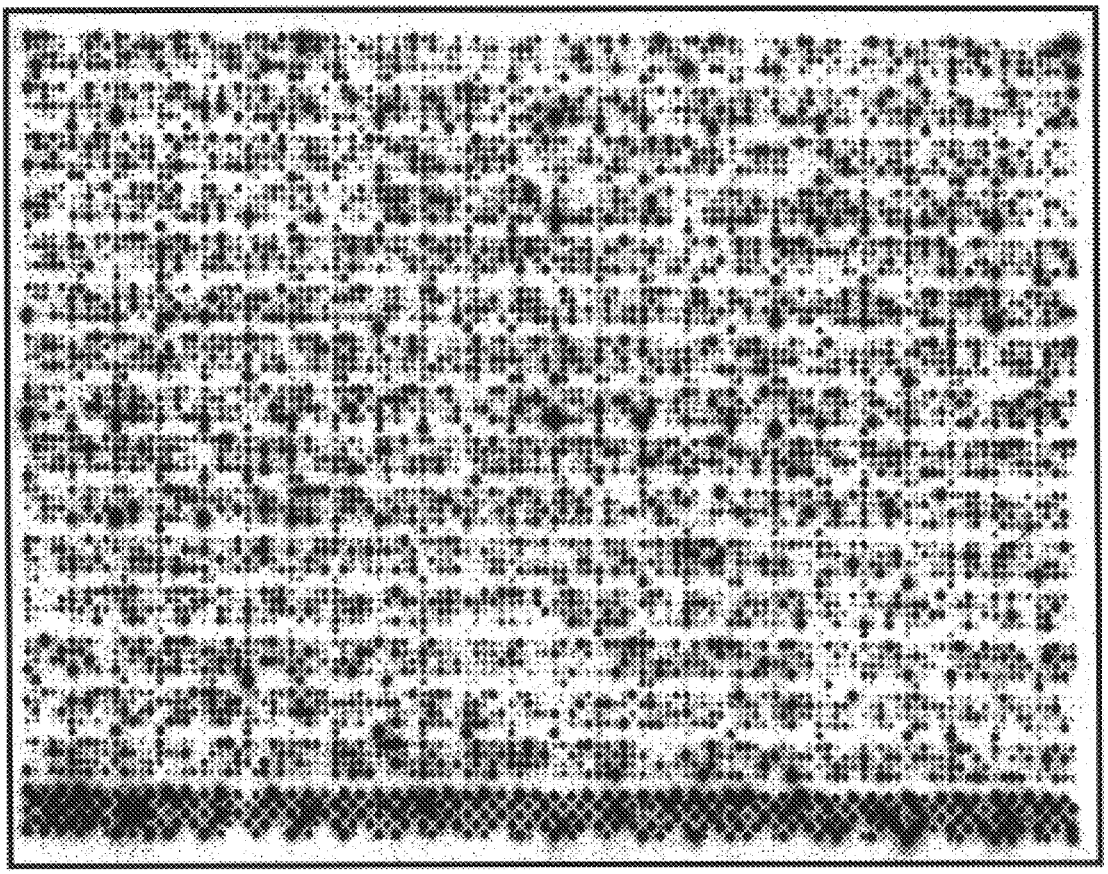
FIG. 4 shows a developed film image of radioactive label for an array with segregated target molecules corresponding to high expressing probes.

This example illustrates the utility of a segregated target array. An array prepared as in Example 2 is used to hybridize with probes prepared as in Example 1. FIG. 4 shows an image of hybridization where hybridization indicia for low density-spaced high expressors are more readily distinguished from each other and the hybridization indicia for high density-spaced low expressors.

What is claimed is:

1. An arrray comprising a set of polynucleotide target molecules immobilized in an array on a surface of a substrate, wherein said target molecules hybridize with a set of labeled/probe molecules expressed by an organism of interest and an measurement of said set of labeled probe molecules provides an indicia of hybridization, wherein the average indicia of hybridization of a subset of said set of probe molecules to a subset of said set of target molecules is at least two times greater than an average indicia of hybridization of said set of labeled probe molecules and wherein said subset of target molecules is segregated in said array at a surface density which is less than 0.5 times the surface density of other target molecules.

2. An array according to claim 1 wherein said first set of target molecules is segregated at a peripheral region of said substrate.

3. An array according to claim 1 wherein said probe molecules are mRNA and said target molecules are single-stranded DNA molecules which are substantially isolated on said array.

4. An array according to claim 1 wherein said organism of interest is a plant selected from the group consisting of *Arabidopsis thaliana*, maize, soy, cotton, wheat, rice, canola and potato.

5. An array according to claim 1 wherein said organism of interest is a fungus, bacterium or virus.

6. An array according to claim 1 wherein said array comprises target molecules of about $10^8$–$10^{11}$ copies of single stranded DNA in deposited elements on a flexible nylon membrane wherein said deposited elements are in rectangular grids of a density of not less than about 100 elements per square centimeter for target molecules except that said subset of target molecules are at a density of not more than about 60 elements per square centimeter.

7. A method for fabricating an array of a set of target molecules which hybridize to labeled probe molecules expressed by an organism of interest wherein the measurement of said set of labeled probe molecules provides an indicia of hybridization, wherein an average indicia of hybridization of a subset of said probes molecules to a subset of said target molecules is at lest two times greater than an average indicia of hybridization, of said set of labeled probe molecules said method comprising (a) depositing the set of target molecules in random spotted elements in a microarray forming a set of random spotted target molecules;

(b) exposing said set of random spotted target molecules under hybridizing conditions to a set of cognate, labeled, probe molecules obtained from the organism under fixed conditions of probe molecule expression;

(c) determining an average indicia of hybridization of said labeled, probe molecules to said target molecules and identifying loci of a subset of said target molecules which when hybridized to probes provide an indicia of hybridization which is at least twice said average indicia of hybridization; and (d) preparing a subsequent array of said set of target molecules immobilized in an array on a solid substrate wherein said subset of target molecules is segregated at a peripheral region of said subsequent array.

* * * * *